United States Patent
Yoo et al.

(10) Patent No.: US 11,805,982 B2
(45) Date of Patent: Nov. 7, 2023

(54) OPTICAL FIBER PROBE AND METHOD FOR MANUFACTURING OPTICAL FIBER PROBE

(71) Applicant: Industry-University Cooperation Foundation Hanyang University, Seoul (KR)

(72) Inventors: Hong Ki Yoo, Seoul (KR); Min Woo Lee, Suwon-si (KR); Jingchao Xing, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 287 days.

(21) Appl. No.: 16/767,910

(22) PCT Filed: Oct. 23, 2018

(86) PCT No.: PCT/KR2018/012535
§ 371 (c)(1),
(2) Date: May 28, 2020

(87) PCT Pub. No.: WO2019/107742
PCT Pub. Date: Jun. 6, 2019

(65) Prior Publication Data
US 2020/0397235 A1   Dec. 24, 2020

(30) Foreign Application Priority Data

Nov. 29, 2017  (KR) .......................... 10-2017-0161247

(51) Int. Cl.
*A61B 1/00*     (2006.01)
*G02B 27/09*    (2006.01)

(52) U.S. Cl.
CPC ........ *A61B 1/00165* (2013.01); *A61B 1/0011* (2013.01); *A61B 1/00188* (2013.01); *G02B 27/095* (2013.01)

(58) Field of Classification Search
CPC . A61B 1/0011; A61B 1/00071; A61B 1/0008; A61B 1/00096; A61B 1/00188; A61B 1/00165; G02B 27/095
See application file for complete search history.

(56) References Cited

U.S. PATENT DOCUMENTS 5,912,764 A    6/1999  Togino
6,445,939 B1*  9/2002  Swanson .............. G02B 6/2552
                                              385/33

(Continued)

FOREIGN PATENT DOCUMENTS

JP   2009-531151 A   9/2009
JP   2012-229976 A   11/2012

(Continued)

OTHER PUBLICATIONS

International Search Report for PCT/KR2018/012535 dated Jan. 21, 2019 (PCT/ISA/210).

*Primary Examiner* — Thomas A Hollweg
*Assistant Examiner* — Mary A El-Shammaa
(74) *Attorney, Agent, or Firm* — Sughrue Mion, PLLC (57) ABSTRACT

Disclosed are an optical fiber probe and a method for manufacturing an optical fiber probe which can reduce astigmatism. The disclosed optical fiber probe comprises: an optical fiber configured to receive light inputted from a light source; a reflection part configured to reflect the inputted light in the direction of a cylindrical surface; and a transparent window comprising an incidence surface and an output surface, the incidence surface coupled to the cylindrical surface of the reflection part, (Continued)

the output surface comprising a curvature thereof different from a curvature of the cylindrical surface.

12 Claims, 6 Drawing Sheets

(56) References Cited

U.S. PATENT DOCUMENTS

| | | | | |
|---|---|---|---|---|
| 9,888,834 B2* | 2/2018 | Buerk | ................ | G02B 23/2423 |
| 2007/0179485 A1* | 8/2007 | Yeik | ................ | A61B 18/24 |
| | | | | 606/15 |
| 2010/0134607 A1* | 6/2010 | Ishihara | ................ | A61B 8/4461 |
| | | | | 348/E7.085 |
| 2010/0253949 A1* | 10/2010 | Adler | ................ | G02B 27/0994 |
| | | | | 385/33 |
| 2013/0107273 A1* | 5/2013 | Dholakia | ........... | G01B 9/02091 |
| | | | | 356/450 |
| 2014/0249419 A1* | 9/2014 | Morita | ................ | A61B 8/4444 |
| | | | | 156/60 |
| 2015/0036146 A1* | 2/2015 | Staloff | ................ | A61B 5/0084 |
| | | | | 356/479 |
| 2015/0079598 A1* | 3/2015 | Yasuda | ................ | B01L 7/52 |
| | | | | 435/6.12 |
| 2015/0133775 A1* | 5/2015 | Kim | ................ | A61B 5/0095 |
| | | | | 600/407 |
| 2017/0322133 A1* | 11/2017 | Trainer | ................ | G01N 21/474 |
| 2022/0031284 A1* | 2/2022 | Takeuchi | ............ | G01S 15/8909 |
| 2022/0043027 A1* | 2/2022 | Hsu | ................ | G01R 1/07342 |

FOREIGN PATENT DOCUMENTS

| | | | | |
|---|---|---|---|---|
| KR | 10-1257100 B1 | | 4/2013 | |
| KR | 10-1637832 B1 | | 7/2016 | |
| WO | WO-0072076 A1 | * | 11/2000 | ............. B82Y 20/00 |
| WO | WO-2016182333 A1 | * | 11/2016 | ............... A61B 1/00 |

* cited by examiner

OPTICAL FIBER PROBE AND METHOD FOR MANUFACTURING OPTICAL FIBER PROBE

CROSS REFERENCE TO RELATED APPLICATIONS

This application is a National Stage of International Application No. PCT/KR2018/012535 filed Oct. 23, 2018, claiming priority based on Korean Patent Application No. 10-2017-0161247, filed Nov. 29, 2017.

BACKGROUND

1. Technical Field

The present invention relates to an optical fiber probe and a method for manufacturing an optical fiber probe, more particularly to an optical fiber probe and a method for manufacturing an optical fiber probe that can reduce astigmatism.

2. Description of the Related Art

Optical fiber probes that can be inserted through tissues are utilized for the purpose of acquiring interstitial images and biometric signals.

For example, optical fiber probes are used to acquire images associated with optical imaging technology such as optical coherence tomography (OCT), confocal microscopy (CM), two-photon microscopy (TPM), multiphoton microscopy (MPM), etc.

SUMMARY OF THE INVENTION

An aspect of the invention provides an optical fiber probe and a method for manufacturing an optical fiber probe that can reduce astigmatism.

An embodiment of the present invention conceived to achieve the objective above provides an optical fiber probe that includes: an optical fiber configured to receive light inputted from a light source; a reflection part configured to reflect the inputted light in the direction of a cylindrical surface; and a transparent window comprising an incidence surface coupled to the cylindrical surface of the reflection part and an output surface comprising a curvature different from the curvature of the cylindrical surface.

Another embodiment of the present invention conceived to achieve the objective above provides an optical fiber probe that includes: an optical fiber configured to receive light inputted from a light source; a first fiber configured to expand the inputted light; a GRIN fiber configured to focus the expanded light; a second fiber comprising a portion polished such that the focused light is reflected totally in the direction of a cylindrical surface; and a transparent window coupled to the cylindrical surface of the second fiber to reduce astigmatism for the totally reflected light.

Still another embodiment of the present invention conceived to achieve the objective above provides a method for manufacturing an optical fiber probe that includes: preparing a resin over a first substrate; contacting a cylindrical surface of an optical fiber probe with the resin, the cylindrical surface configured to output light inputted to the optical fiber probe; hardening the resin while the resin is in contact with the cylindrical surface; and separating the optical fiber probe from the substrate.

The present invention can reduce astigmatism caused by a cylindrical surface, through which light passes, by coupling a transparent window to the transparent window.

Also, the present invention can reduce astigmatism caused by the cylindrical surface through which light passes to thereby reduce the spot size of the focus in a lateral direction and increase resolution in the lateral direction.

Also, the present invention can improve the optical efficiency of the optical fiber probe and reduce noise in images incurred by reflection.

DETAILED DESCRIPTION OF THE INVENTION

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the drawings, similar reference numerals are used for similar elements.

Certain embodiments of the present invention are described below in more detail with reference to the accompanying drawings.

Figure 1:
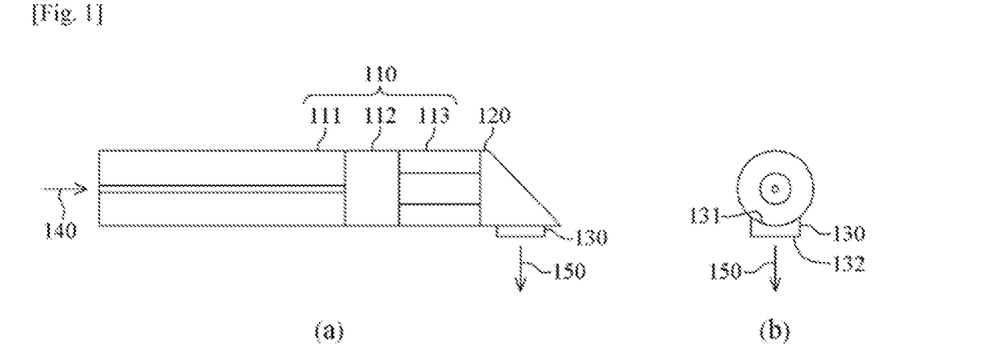
FIG. 1 illustrates an optical fiber probe according to an embodiment of the present invention.
Figure 2:
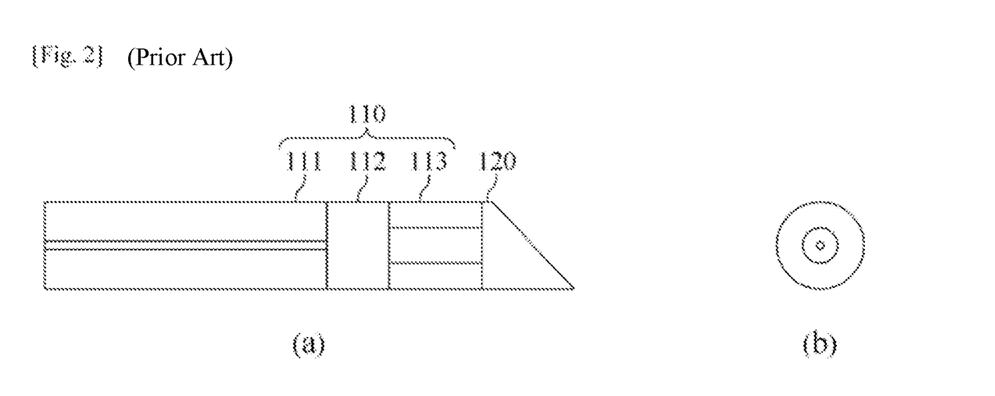
FIG. 2 illustrates an optical fiber probe according to the related art.
Figure 3:
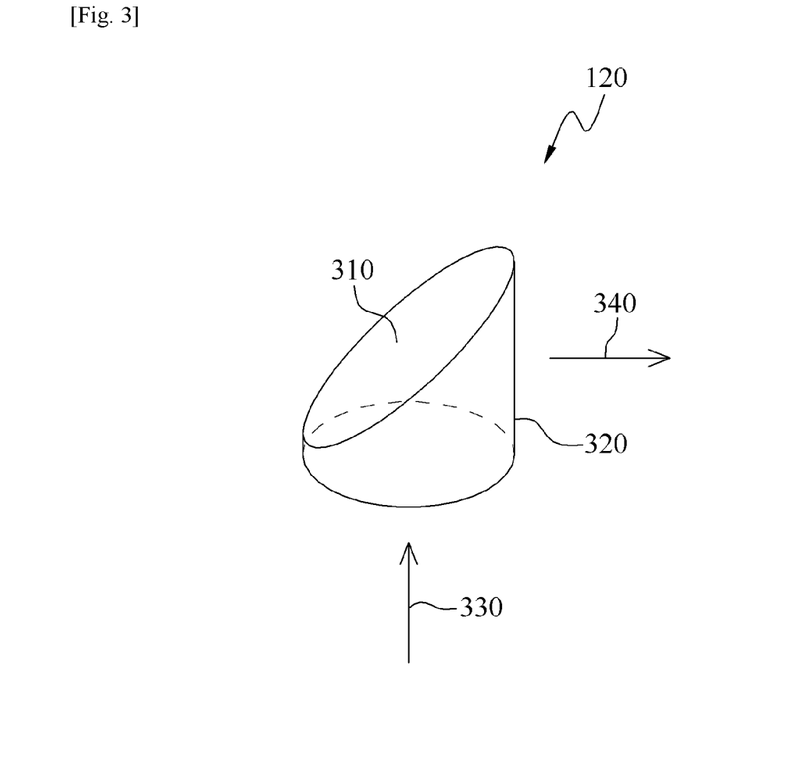
FIG. 3 illustrates the reflection part of an optical fiber probe.

FIG. 1 illustrates an optical fiber probe according to an embodiment of the present invention, and FIG. 2 illustrates an optical fiber probe according to the related art. FIG. 3 illustrates the reflection part of an optical fiber probe. FIG. 1(a) and FIG. 2(a) illustrate side views of the optical fiber probes, while FIG. 1(b) and FIG. 2(b) illustrate front views of the optical fiber probes.

Referring to FIG. 1, an optical fiber probe based on the present invention may include an optical fiber 110, a reflection part 120, and a transparent window 130.

When light from a light source is inputted 140 to the optical fiber 110, the inputted light may be reflected at the reflection part 120 to be outputted 150 in a sideward direction of the reflection part 120. The optical fiber 110 can include, for example, a single mode fiber (SMF) 111, a no-core fiber (NCF) 112, and a GRIN fiber 113. A no-core fiber 112 receives light that has been inputted to the single mode fiber 111 and expands the inputted light, and the GRIN fiber 113 receives the light expanded by the no-core fiber 112 to focus the expanded light. In certain embodiments, various optical components for expanding and focusing light, other than the no-core fiber 112 and the GRIN fiber 113, can be used, and the inputted light can be expanded by a multi-mode fiber (MMF).

The reflection part 120 may reflect the light inputted 330 to the optical fiber 110 in the direction of the cylindrical surface 320. As illustrated in FIG. 3, the reflection part 120 can have a cylindrical shape with a certain portion polished, and light can be reflected by the polished reflector surface 310 to be outputted 340 in the direction of the cylindrical surface 320. The reflector surface 310 can be formed by polishing, such that light focused by the GRIN fiber 113 can be reflected totally, and for example can be of a form achieved by polishing a no-core fiber or a multi-mode fiber. Alternatively, a reflection layer can be formed at the reflector surface 310 such that the light focused at the GRIN fiber 113 can be reflected in the direction of the cylindrical surface 320.

The light reflected at the reflection part 120 may be inputted to the transparent window 130. The transparent window 130 may include an input surface 131, which may be coupled to the cylindrical surface 320 of the reflection part 120, and an output surface 132, which may have a curvature different from the curvature of the cylindrical surface 320, and may be the part included additionally compared to the optical fiber probe of the related art shown in FIG. 2.

Since the reflection part 120 has a cylindrical shape with a portion thereof polished off, the light outputted from the reflection part 120 may pass through the cylindrical surface 320, and ultimately, the final effect is tantamount to the light outputted from the reflection part 120 passing through a cylindrical lens. As a cylindrical lens may cause astigmatism, the present invention proposes a way to reduce astigmatism by using a transparent window.

FIG. 1 illustrates an example in which the output surface 132 has a flat shape. The input surface 131 may be shaped as a curved surface similar to the cylindrical surface 320, but the output surface 132 may be shaped as a flat plane having a curvature of infinite. In different embodiments, the curvature and shape of the output surface 132 can take various values, and the output surface 132 can be of a convex shape with a curvature smaller than the curvature of the cylindrical surface 320 of the reflection part 120. Ultimately, the astigmatism caused by the cylindrical surface 320 of the reflection part 120 can be alleviated by the transparent window 130 by an amount corresponding to the difference in radii of curvature between the cylindrical surface 320 and the output surface 132.

In one example, an optical fiber probe based on the present invention can be inserted through tissues while inserted in a transparent tube for protection from bodily fluids during insertion through tissues, and the transparent tube itself can serve as a cylindrical lens. As such, according to another embodiment of the present invention, the output surface 132 can have a concave form to offset the astigmatism resulting from not only the reflection part 120 but also the transparent tube.

The transparent window 130 can be manufactured from not only glass but any of a variety of transparent materials and can be manufactured from a transparent resin group for convenient manufacture. The transparent window 130 can be, for example, of an epoxy resin material.

Thus, according to the present invention, a transparent window can be coupled to a cylindrical surface through which light may pass, whereby the astigmatism occurring at the cylindrical surface can be reduced.

According to another embodiment of the present invention, various patterns can be formed on the output surface 132 of the transparent window 130, where such patterns can act as a phase modulator. Such a pattern can increase the focal depth or reduce the spot size of the focus, to enhance lateral resolution.

Figure 4:
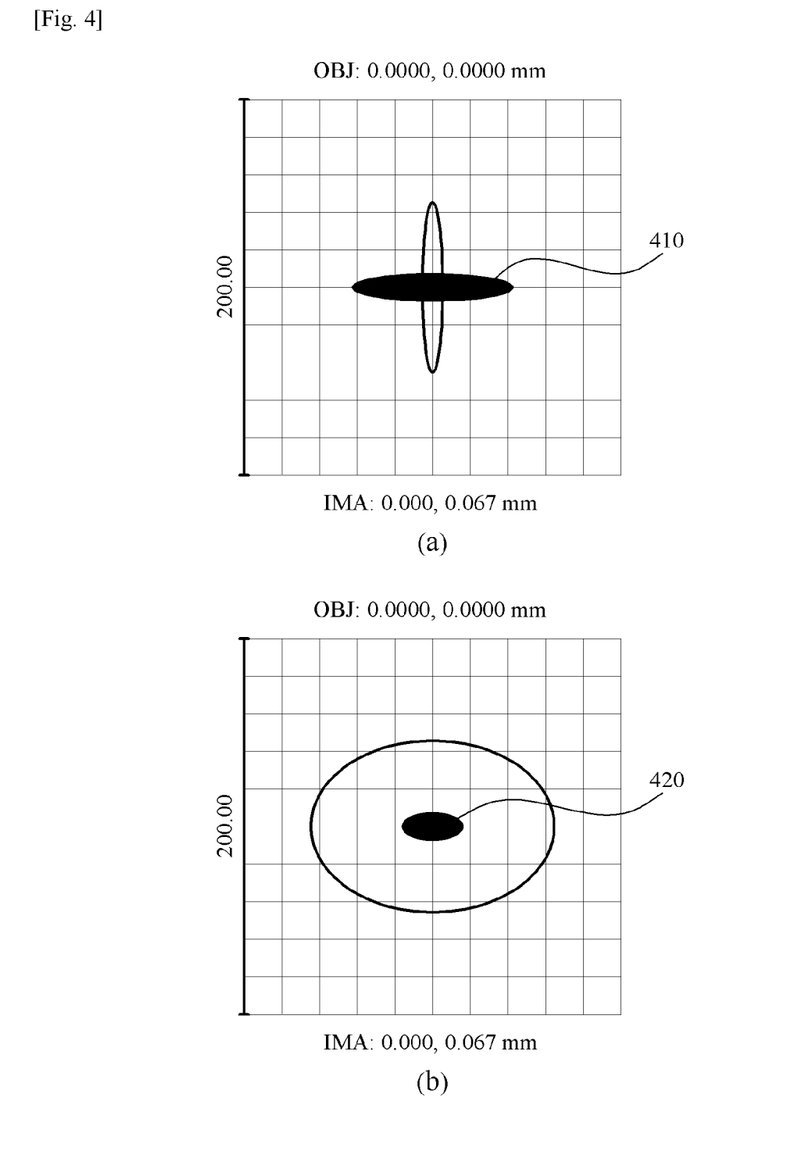
FIG. 4 shows spot diagrams for a focus formed by an optical fiber probe according to an embodiment of the present invention.

FIG. 4 shows spot diagrams for a focus formed by an optical fiber probe according to an embodiment of the present invention. FIG. 4(a) shows a spot diagram for an optical fiber probe that does not use a transparent window, and FIG. 4(b) shows a spot diagram for an optical fiber probe in which the output surface uses a flat transparent window.

Astigmatism can cause an increase in the spot size of a focus in the lateral direction, but it can be seen that the spot size 420 in FIG. 4(b) is considerably smaller than the spot size 410 in FIG. 4(a). In other words, using an optical fiber probe based on the present invention can reduce the astigmatism occurring at the cylindrical surface.

Depending on the usage environment, such as in regard to using a transparent tube, etc., greater reductions in astigmatism can be achieved when the output surface of the transparent window is formed in a concave shape, and the curvature of the output surface can be determined according to the usage environment or the design parameters, etc., of the optical fiber probe.

Thus, according to the present invention, the astigmatism caused by the cylindrical surface can be reduced, and the lateral resolution can be increased as the spot size of the focus in the lateral direction is reduced.

Figure 5:
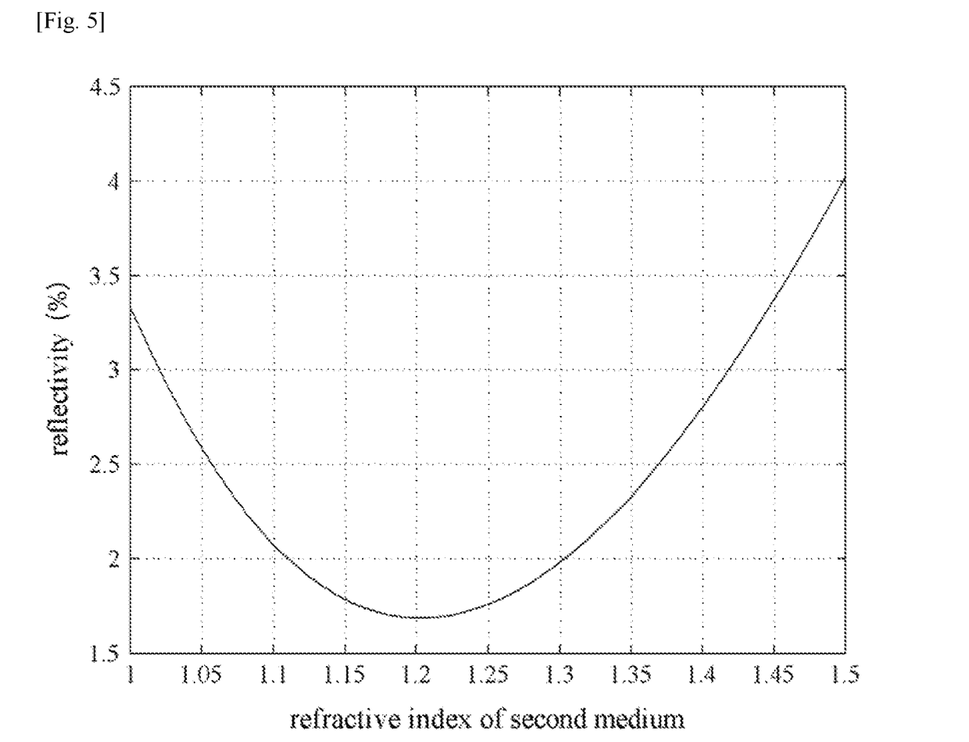
FIG. 5 is a graph plotting reflection rate according to the refractive index of a transparent window in an embodiment of the present invention.

FIG. 5 is a graph plotting reflectivity according to the refractive index of a transparent window in an embodiment of the present invention.

When light passes through two media having different refractive indexes, light can be reflected at the interface between the two media, where the reflectivity may be determined by the refractive indexes of the two media. When light approaches the interface between two media from a perpendicular direction, the reflectivity r may be determined as [Equation 1] below. In [Equation 1], $n_1$ represents the refractive index of a first medium, and $n_2$ represents the refractive index of a second medium.

$$r = \left(\frac{n_1 - n_2}{n_1 + n_2}\right)^2 \quad \text{[Equation 1]}$$

In an optical fiber probe, the no-core fiber (first medium) and the air (second medium) outside the no-core fiber that can be used for the reflection part generally have refractive indexes of 1.4468 and 1, respectively, so that the reflectivity calculated by [Equation 1] is 3.3%.

That is, in cases where a transparent window is not used, the reflectivity for the light may be about 3.3%, but the reflectivity for the light resulting from the transparent window according to the present invention can be further reduced. In cases where a transparent window is used, i.e. when a new medium is added between the no-core fiber and the air, the reflectivity for the light can be calculated as [Equation 2] below, and as the refractive index of the transparent window is varied, the reflectivity for the light can be varied as well.

$$r = \left(\frac{n_1 - n_2}{n_1 + n_2}\right)^2 + \left(1 - \left(\frac{n_1 - n_2}{n_1 + n_2}\right)^2\right) \cdot \left(\frac{n_2 - n_3}{n_2 + n_3}\right)^2 \quad \text{[Equation 2]}$$

Here, $n_1$ represents the refractive index of a first medium (no-core fiber), $n_2$ represents the refractive index of a second medium (transparent window), and $n_3$ represents the refractive index of a third medium (air).

FIG. 5 shows the reflectivity obtained according to the refractive index of the transparent window, where it can be seen that a minimum reflectivity of 1.68% can be obtained when the refractive index of the transparent window is about 1.2. Therefore, by determining the refractive index of the transparent window based on the refractive indexes of the reflection part and air such that the reflectivity is reduced, and then manufacturing the transparent window and coupling to the reflection part, it is possible to enhance the optical efficiency of the optical fiber probe and also reduce noise in the image that may otherwise occur due to reflection.

Figure 6:
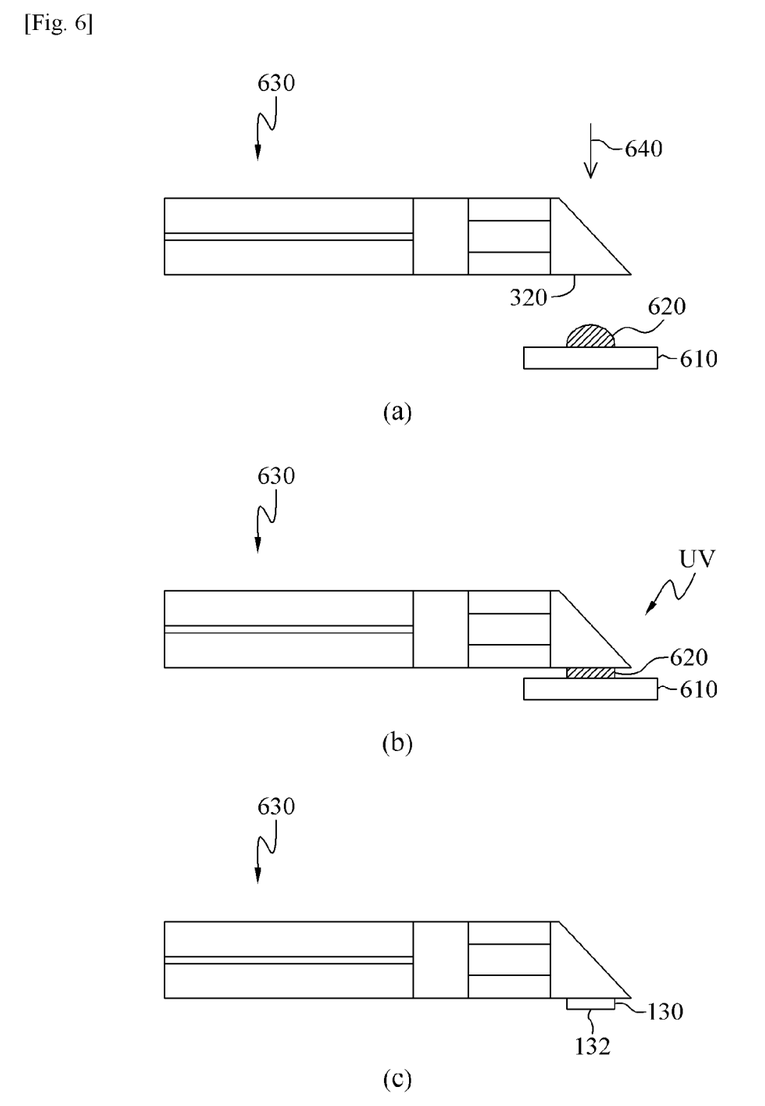
FIG. 6 shows diagrams illustrating a method for manufacturing an optical fiber probe according to an embodiment of the present invention.
Figure 7:
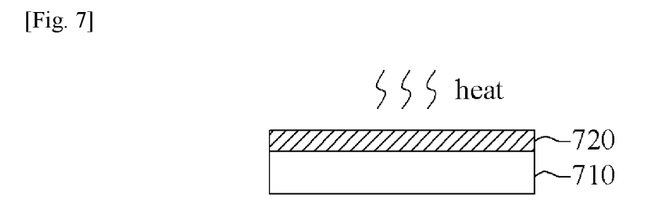
FIG. 7 shows a diagram illustrating a method for manufacturing an optical fiber probe according to another embodiment of the present invention.

FIG. 6 shows diagrams illustrating a method for manufacturing an optical fiber probe according to an embodiment of the present invention, and FIG. 7 shows a diagram illustrating a method for manufacturing an optical fiber probe according to another embodiment of the present invention.

Referring to FIG. 6(a), a resin 620 may be prepared over a first substrate 610, and the cylindrical surface 320 of the optical fiber probe 630 through which the inputted light is outputted may be placed in contact with the resin 620. The first substrate 610 can have a flat shape but, depending on the embodiment, can have a convex shape or a concave shape, with the curvature selected from various values. The optical fiber probe 630 can be the optical fiber probe illustrated in FIG. 2, and the resin 620 can be an epoxy resin and a UV-curable resin.

Referring to FIG. 6(b), while the cylindrical surface 320 and the resin 620 are in contact with each other, the resin 620 can be hardened, where UV rays can be irradiated onto the resin 620 to harden the resin 620.

Referring to FIG. 6(c), when the hardening of the resin 620 is completed, the optical fiber probe 630 may be separated from the first substrate 610, where the hardened resin may correspond to the transparent window 130 described above. The output surface 132 of the transparent window 130 that was placed in contact with the flat first substrate 610 can also be formed in a flat shape, and the input surface of the transparent window 130 may be coupled and secured to the reflection part. In cases where the first substrate 610 is of a convex shape, the output surface 132 can become concave, and in cases where the first substrate 610 is of a concave shape, the output surface 132 can become convex.

According to an embodiment of the present invention, the amount of resin 620 provided over the first substrate 610 can be determined based on the beam width of the light outputted through the cylindrical surface 320. For example, if the beam width is wide, the width of the transparent window 130 would also need to be wide, and therefore it may be preferable to increase the amount of resin 620 provided on the first substrate 610. Also, as it is possible to apply pressure 640 after placing the optical fiber probe 630 and the resin 620 in contact with each other, the width of the transparent window 130 can be increased by increasing the applied pressure 640 so that the contact area between the resin 620 and the cylindrical surface 320 may be increased.

The first substrate 610 can be a silicon wafer substrate, and when the resin 620 is hardened, the resin 620 may adhere not only to the reflection part but also to the first substrate 610, making it difficult to separate the optical fiber probe from the substrate. As such, it is possible to manufacture the optical fiber probe by having a coating agent for preventing adhesion between the resin 620 and first substrate 610 coated onto the first substrate 610.

Alternatively, as illustrated in FIG. 7, polydimethylsiloxane (PDMS) can be used for the first substrate. A flat PDMS substrate can be obtained by coating PDMS 720 in a liquid state onto a flat second substrate 710 and then applying heat to harden the coated PDMS 720. The shape of the second substrate can be convex or concave depending on the embodiment, and likewise the shape of the PDMS substrate can also be convex or concave depending on the shape of the second substrate.

In certain embodiments, a preconfigured pattern can be formed on the second substrate, so that the pattern of the second substrate forms a pattern on the PDMS substrate as well. Thus, a pattern can ultimately be formed on the output surface of the transparent window as well. Such a pattern may function as a phase modulator.

While the present invention is described above by way of limited embodiments and drawings that refer to particular details such as specific elements, etc., these are provided only to aid the general understanding of the present invention. The present invention is not to be limited by the embodiments above, and the person having ordinary skill in the field of art to which the present invention pertains would be able to derive numerous modifications and variations from the descriptions and drawings above. Therefore, it should be appreciated that the spirit of the present invention is not limited to the embodiments described above. Rather, the concepts set forth in the appended scope of claims as well as their equivalents and variations are encompassed within the spirit of the present invention.

What is claimed is:

1. An optical fiber probe comprising:
an optical fiber configured to receive light inputted from a light source;
a reflection part configured to reflect the inputted light in the direction of a cylindrical surface; and
a transparent window comprising an incidence surface and an output surface, the incidence surface coupled to the cylindrical surface of the reflection part, the output surface comprising a curvature thereof different from a curvature of the cylindrical surface,
wherein the output surface comprises a concave shape or a convex shape with a curvature smaller than the curvature of the cylindrical surface, and
wherein a refractive index of the transparent window is determined by refractive indexes of the reflection part and air such that the reflection of the light is reduced at the interface between the reflection part and the transparent window, and the interface between the transparent window and air.

2. The optical fiber probe of claim 1, wherein the reflection part is a no-core fiber comprising a portion thereof polished such that the focused light undergoes total reflection.

3. The optical fiber probe of claim 1, wherein the reflection part comprises a reflection layer configured to reflect the focused light.

4. The optical fiber probe of claim 1, wherein the transparent window is of an epoxy resin material.

5. An optical fiber probe comprising:
an optical fiber configured to receive light inputted from a light source;
a first fiber configured to expand the inputted light;
a GRIN fiber configured to focus the expanded light;

a second fiber comprising a portion thereof polished such that the focused light is reflected totally in the direction of a cylindrical surface; and a transparent window coupled to the cylindrical surface of the second fiber and configured to reduce astigmatism for the totally reflected light, wherein the transparent window comprises an incidence surface and an output surface, the incidence surface coupled to the cylindrical surface, the output surface comprising a curvature different from a curvature of the cylindrical surface, wherein the output surface comprises a concave shape or a convex shape with a curvature smaller than the curvature of the cylindrical surface, and wherein a refractive index of the transparent window is determined by refractive indexes of the reflection part and air such that the reflection of the light is reduced at the interface between the reflection part and the transparent window, and the interface between the transparent window and air.

6. The optical fiber probe of claim 5, wherein the first and second fibers are no-core fibers or multi-mode fibers.

7. A method for manufacturing an optical fiber probe, the method comprising:
preparing a resin over a first substrate;
contacting a cylindrical surface of an optical fiber probe with the resin, the cylindrical surface configured to output light inputted to the optical fiber probe;
hardening the resin while the resin is in contact with the cylindrical surface; and
separating the optical fiber probe from the first substrate;
coating a PDMS in a liquid state onto a second substrate; and
manufacturing the first substrate by hardening the PDMS, wherein the second substrate comprises a concave shape or a convex shape with a curvature smaller than the curvature of the cylindrical surface.

8. The method for manufacturing an optical fiber probe according to claim 7, wherein an amount of the resin prepared over the first substrate is determined based on a beam width of light outputted through the cylindrical surface.

9. The method for manufacturing an optical fiber probe according to claim 7, wherein the resin is an epoxy resin.

10. A method for manufacturing an optical fiber probe, the method comprising:
preparing a resin over a first substrate;
contacting a cylindrical surface of an optical fiber probe with the resin, the cylindrical surface configured to output light inputted to the optical fiber probe;
hardening the resin while the resin is in contact with the cylindrical surface; and
separating the optical fiber probe from the first substrate,
wherein the first substrate comprises a coating agent coated thereon, the coating agent configured to prevent adhesion between the resin and the first substrate, and
the first substrate comprises a concave shape or a convex shape with a curvature smaller than the curvature of the cylindrical surface.

11. The method for manufacturing an optical fiber probe according to claim 10, wherein an amount of the resin prepared over the first substrate is determined based on a beam width of light outputted through the cylindrical surface.

12. The method for manufacturing an optical fiber probe according to claim 10, wherein the resin is an epoxy resin.

* * * * *